(12) United States Patent
Vickers

(10) Patent No.: US 9,284,841 B1
(45) Date of Patent: Mar. 15, 2016

(54) DISPOSABLE HEAT EXCHANGER ASSEMBLY FOR STERILE AND ASEPTIC BIOTECHNOLOGY AND PHARMACEUTICAL MANUFACTURING APPLICATIONS

(76) Inventor: Julie C. Vickers, Cumberland, RI (US)

(*) Notice: Subject to any disclaimer, the term of this patent is extended or adjusted under 35 U.S.C. 154(b) by 70 days.

(21) Appl. No.: 13/331,083

(22) Filed: Dec. 20, 2011

Related U.S. Application Data

(60) Provisional application No. 61/507,837, filed on Jul. 14, 2011.

(51) Int. Cl.
| | |
|---|---|
| *F28F 7/00* | (2006.01) |
| *F28D 15/00* | (2006.01) |
| *F28F 3/00* | (2006.01) |
| *F01C 19/10* | (2006.01) |

(52) U.S. Cl.
CPC ..................... *F01C 19/10* (2013.01)

(58) Field of Classification Search
CPC ............. A61F 2007/0222; A61F 2007/022; F28D 9/0037; F28D 9/005; F28D 9/0056
USPC ................... 165/46, 104.14, 166, 185
See application file for complete search history.

(56) References Cited

U.S. PATENT DOCUMENTS

| | | | | |
|---|---|---|---|---|
| 2,582,871 | A * | 1/1952 | Kintner ........................... | 165/70 |
| 3,842,617 | A | 10/1974 | Chase et al. | |
| 4,731,072 | A * | 3/1988 | Aid ................................. | 604/408 |
| 4,744,414 | A * | 5/1988 | Schon ............................. | 165/167 |
| 4,907,308 | A * | 3/1990 | Leininger ..................... | A61F 7/00 165/46 |
| 4,982,785 | A * | 1/1991 | Tomlinson .................. | F24H 3/105 126/110 R |
| 5,245,693 | A | 9/1993 | Ford et al. | |
| 5,254,094 | A * | 10/1993 | Starkey ..................... | A61M 5/44 604/113 |
| 6,572,641 | B2 * | 6/2003 | Brugger .................. | A61F 7/0085 607/106 |
| 7,647,897 | B2 * | 1/2010 | Ootomo ..................... | F24H 1/40 122/31.1 |
| 7,833,206 | B1 | 11/2010 | Lumpkin et al. | |
| 8,015,950 | B2 * | 9/2011 | Okamoto .................. | F24H 1/145 122/31.1 |
| 8,292,594 | B2 * | 10/2012 | Tracey ..................... | A61M 1/369 417/395 |
| 2004/0190884 | A1 * | 9/2004 | Stewart ................... | A61M 5/445 392/470 |
| 2006/0168987 | A1 * | 8/2006 | Kyees ..................... | B67D 1/0862 62/390 |
| 2007/0278155 | A1 * | 12/2007 | Lo .......................... | A61M 1/16 210/646 |
| 2008/0031773 | A1 * | 2/2008 | Eccleston ............... | A61M 1/3666 422/44 |
| 2008/0262409 | A1 | 10/2008 | Derrico et al. | |
| 2009/0012456 | A1 * | 1/2009 | Childers ................. | A61M 1/288 604/29 |
| 2009/0242173 | A1 * | 10/2009 | Mitchell ................. | C12M 23/14 34/402 |
| 2011/0022047 | A1 * | 1/2011 | Buysse ................... | G05D 23/19 606/45 |
| 2014/0178983 | A1 * | 6/2014 | Staheli ................... | B01F 3/04241 435/325 |

* cited by examiner

*Primary Examiner* — Frantz Jules
*Assistant Examiner* — Claire Rojohn, III
(74) *Attorney, Agent, or Firm* — Barlow, Josephs & Holmes, Ltd.

(57) ABSTRACT

A disposable heat exchanger system including a sterile disposable bag assembly and sets of modular stainless steel heating/cooling plate assemblies is disclosed. The sterile disposable bags are manifolded together via disposable tubing and are installed and filled in place with cell culture or protein containing process fluid between the stainless steel heating/cooling plates. The stainless steel heating/cooling plates are manifolded together in a modular fashion with stainless steel tubing. Both the sterile disposable bag assembly and the heating/cooling plates are configured to have a serpentine flow pattern. The process fluid within the sterile disposable bag assembly and heating/cooling fluid within the modular stainless steel heating/cooling plates flow in opposite directions in order to provide counter-current flow for efficient heating or cooling.

19 Claims, 8 Drawing Sheets

HEAT EXCHANGER SHELL
MANIFOLD ASSEMBLY

DISPOSABLE HEAT EXCHANGER
ASSEMBLY (BAGS FILLED) SIDE VIEW

DISPOSABLE BAG
FRONT VIEW

HEAT EXCHANGER SHELL
FRONT VIEW

DISPOSABLE BAG
MANIFOLD ASSEMBLY

HEAT EXCHANGER SHELL
MANIFOLD ASSEMBLY

HEAT EXCHANGER SHELL
CROSS SECTION

DISPOSABLE HEAT EXCHANGER
ASSEMBLY (BAGS FILLED) SIDE VIEW

DISPOSABLE HEAT EXCHANGER ASSEMBLY FOR STERILE AND ASEPTIC BIOTECHNOLOGY AND PHARMACEUTICAL MANUFACTURING APPLICATIONS

RELATED CASES

Priority for this application is hereby claimed under 35 U.S.C. §119(e) to commonly owned and U.S. Provisional Patent Application No. 61/507,837 which was filed on Jul. 14, 2011 and which is incorporated by reference herein in its entirety.

FIELD OF THE INVENTION

The invention relates generally to biotechnology and pharmaceutical manufacturing applications where disposable components are utilized for sterile and aseptic cell culture or protein purification processing.

BACKGROUND OF THE INVENTION

In the biotechnology and pharmaceutical manufacturing industries, disposable bags and tubing assemblies are sometimes used in lieu of metallic equipment and piping for aseptic or sterile processing. Disposable bags and tubing assemblies are used because they do not require cleaning or steaming in place as do metallic equipment and piping to maintain cleanliness and/or sterility. The disposable components are preferred because they can be sterilized via gamma-irradiation and discarded after use.

To date, an efficient disposable method for heating or cooling cell culture or protein purification process fluid does not exist. Large jacketed disposable bag holders or stainless steel heat exchangers are typically used. In many cases, temperature is not well controlled causing quality or yield issues.

Accordingly, it is an object of the present invention to provide an improved method and apparatus for heating or cooling cell culture or protein purification process fluid.

Another object of the present invention is to provide a disposable heat exchanger system integrating a sterile disposable bag assembly with a heat exchanger manifold assembly.

Still another object of the present invention is to provide an improved method and apparatus that in accordance with the foregoing objects and that provides enhanced quality and yield in cell culture and protein purification applications.

BRIEF SUMMARY OF THE INVENTION

In accordance with the present invention, there is provided a disposable heat exchanger system comprised of a sterile disposable bag assembly and sets of modular stainless steel heating/cooling plates. The sterile disposable bags are manifolded together via disposable tubing and are installed and filled in place with cell culture or protein containing process fluid within the stainless steel heating/cooling plates. The stainless steel heating/cooling plates are manifolded together in a modular fashion with stainless steel tubing.

Both the disposable bag assemblies and the heating/cooling plates are configured to have a serpentine flow pattern. The process fluid within the sterile disposable bag assembly and heating/cooling fluid within the modular stainless steel heating/cooling plates flow in opposite directions in order to provide counter-current flow for efficient heating or cooling. The sterile disposable bag assemblies are filled in place within the plates via the bottom process inlet port on the first bag in the disposable bag manifold series. The disposable bags are filled in place from bottom to top with process fluid where all air within the bags is displaced as they fill. Once the first bag of the bag manifold series is filled, the disposable interconnecting tubing allows the process fluid to cascade to the next bag in the series. As the cell culture or protein containing fluid flows through the disposable bags, a tight fit is formed within the stainless steel plates to maximize the heat transfer area. This pattern continues until all bags are filled and the process fluid then exits via the top process outlet port of the last bag in the disposable bag manifold series. The flow of the process fluid continues through this path during normal operation. The heating/cooling fluid flows in the opposite direction through the stainless steel plates where the heating/cooling fluid enters via the top stainless steel heat transfer fluid inlet port on the last stainless steel plate in the heat exchanger shell manifold assembly. The heating/cooling fluid then flows through the stainless steel plates in series from top to bottom via the stainless steel interconnecting tubing to provide counter-current flow. The heat transfer fluid then exits via the bottom stainless steel heat transfer outlet port. The flow of the heat transfer fluid continues through this opposing path during normal operation.

BRIEF DESCRIPTION OF THE DRAWINGS

It should be understood that the drawings are provided for the purpose of illustration only and are not intended to define the limits of the disclosure. In the drawings depicting the present invention, all dimensions are to scale. The foregoing and other objects and advantages of the embodiments described herein will become apparent with reference to the following detailed description when taken in conjunction with the accompanying drawings in which.

DETAILED DESCRIPTION

In this disclosure, numerous specific details are set forth to provide a sufficient understanding of the present invention. Those skilled in the art, however, will appreciate that the present invention may be practiced without such specific details. In other instances, well-known elements have been illustrated in order not to obscure the present invention in unnecessary detail. Additionally, some details have been omitted inasmuch as such details are not considered necessary to obtain a complete understanding of the present invention, and are considered to be within the understanding of persons of ordinary skill in the relevant art.

Figure 1:
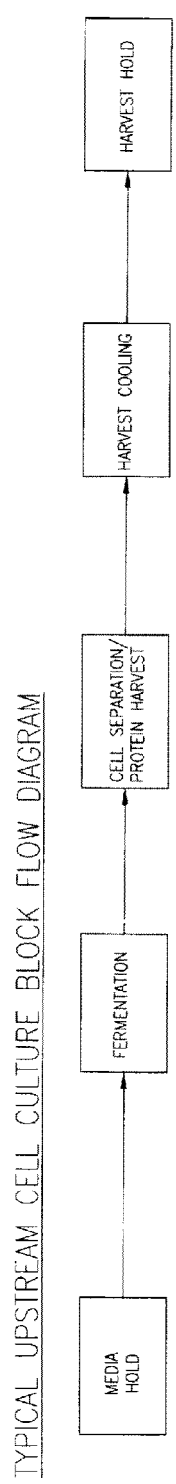
FIG. 1 illustrates typical sterile or aseptic cell culture processing schemes and shows how the disposable heat exchanger of the present invention is used in such applications.
Figure 1:
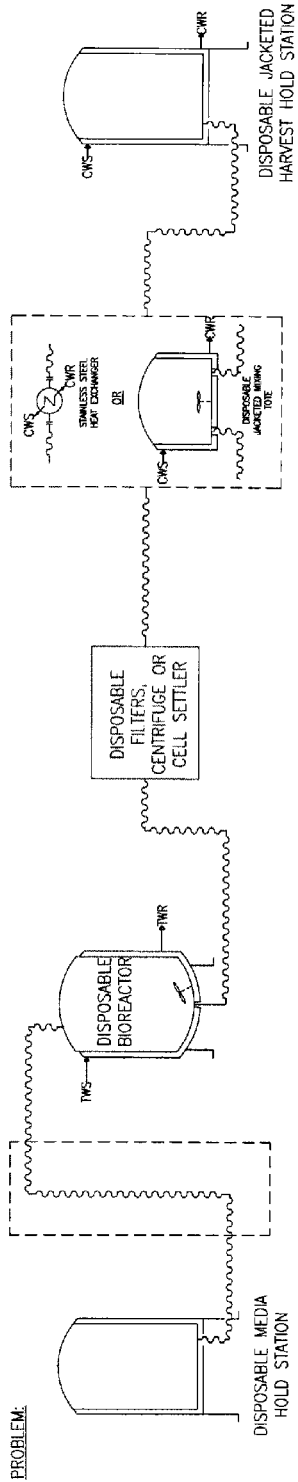
Figure 1:
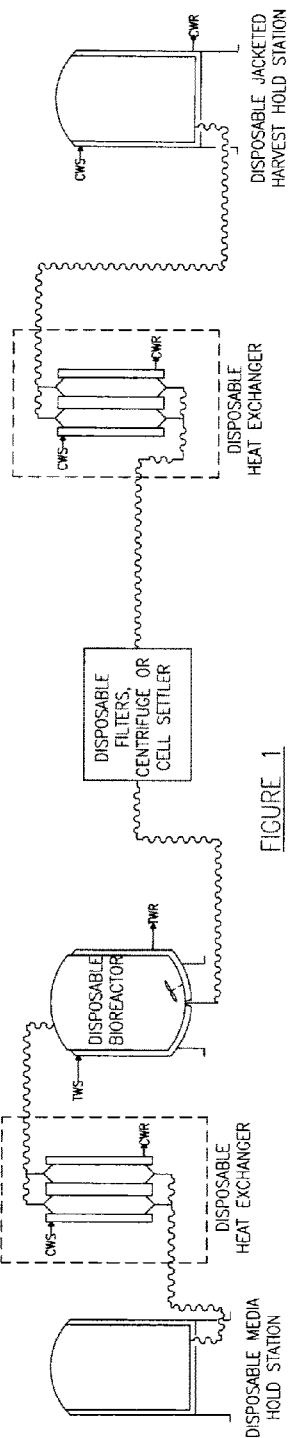
Figure 2:
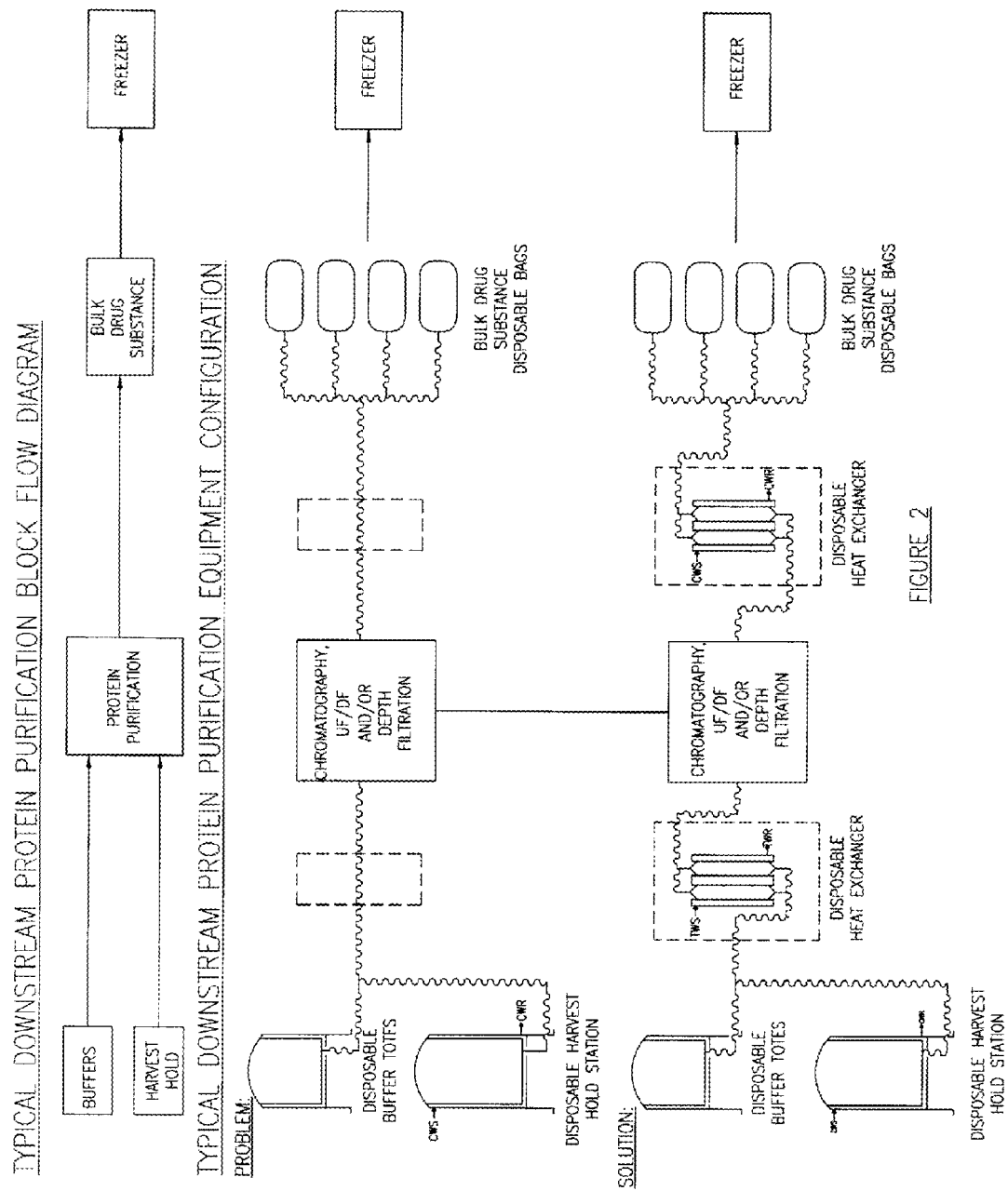
FIG. 2 illustrates typical sterile or aseptic protein purification processing schemes and shows how the disposable heat exchanger of the present invention is used in such applications.

FIGS. 1 and 2 demonstrate typical cell culture and protein purification block flow diagrams with corresponding examples of typical disposable equipment configurations. In FIG. 1 the top diagram depicts a typical upstream cell culture block flow diagram, while in FIG. 2 the top diagram depicts a typical downstream protein purification block flow diagram. The middle diagrams in both FIGS. 1 and 2 depict the respective "Problem" configuration. The "Problem" equipment configuration in each figure shows typical equipment configurations using existing disposable technology. The bottom diagrams in both FIGS. 1 and 2 depict the respective "Solution" configuration. The "Solution" equipment configurations demonstrate how the invention herein may be applied to solve such problems by providing efficient heat transfer and optimal temperature control using disposable features.

As depicted in FIG. 1, the "Problem" equipment configuration shows there is currently no method to efficiently heat cell culture media prior to bioreactor inoculation or during a perfusion cell culture process. Currently, for batch processes, cold or room temperature media is stored in a Disposable Media Hold Station and transferred to a Disposable Bioreactor where the media is heated prior to inoculation. The heating of media in the Disposable Bioreactor takes several hours and is far less efficient than heating with a heat exchanger. As shown in the "Solution" equipment configuration, the invention herein would be applied to save time in heating media prior to inoculation. In a perfusion process, cell culture media is continuously added to the Disposable Bioreactor as the cell culture grows and/or protein is harvested. Adding cold or room temperature media directly to the Disposable Bioreactor is not optimal for the cell culture process as it may affect cell culture growth and/or protein production. The invention herein would be applied to heat the cell culture media as it is transferred into the Disposable Bioreactor to promote optimal cell growth and protein production.

Also depicted in FIG. 1, the "Problem" equipment configuration shows there is currently no method to efficiently cool harvested protein using existing disposable technology. Existing technology is limited to large disposable mixing totes or stainless steel heat exchangers. Large disposable mixing totes are not optimal as they are not efficient for heat transfer in a continuous process and have excessive hold-up volume where expensive product is wasted, ultimately affecting yield. Stainless steel heat exchangers are not preferred because they must be cleaned and steamed in or out of place for aseptic and/or sterile use and must be maintained for cleanliness and sterility. As shown in the "Solution" equipment configuration, the invention herein would be applied to efficiently cool the harvested protein in an efficient, disposable fashion with minimal hold-up volume.

In FIG. 2, the "Problem" equipment configuration shows there is currently no disposable method of controlling temperature for harvested protein and buffers required for various protein purification steps. The protein containing harvest fluid and buffers are typically left at room temperature prior to most purification steps. Because of variations in environmental conditions where the fluids are stored, temperature differences during protein purification steps can cause quality and yield issues with respect to filtration and especially chromatography column adsorption and/or stripping. As shown in the "Solution" equipment configuration, the invention herein would be applied to efficiently regulate the temperature of the harvested protein and/or buffers in an efficient, disposable fashion.

Also depicted in FIG. 2, the "Problem" equipment configuration shows there is currently no disposable method of efficiently cooling the bulk drug substance intermediate prior to freezer storage. When bulk drug substance intermediates are left at ambient or uncontrolled temperatures for long periods of time, they lose their strength and efficacy very quickly. In addition, cooling disposable bulk intermediate containers in a freezer is an inefficient heat transfer method. As shown in the "Solution" equipment configuration, the invention herein would be applied to efficiently cool the bulk drug substance intermediate prior to freezer storage potentially preserving the yield, strength and efficacy of the product.

FIG. 3 illustrates the disposable heat exchanger assembly constructed in accordance with the principles of this invention. As shown in FIG. 3, the disposable heat exchanger assembly comprises a series of stainless steel sealed plate members 1 each with internal welds W to form a serpentine pathway with a dimpled heat transfer surface. In FIGS. 3B and 3D the arrows A1 indicate this serpentine flow path. The welds W extend substantially in parallel and are spaced apart leaving gaps to define this serpentine flow pattern. The stainless steel sealed plate members 1 are joined together by a stainless steel interconnecting tubing 9 to form the heat exchanger shell manifold assembly 2, as depicted in FIG. 3D. As shown also in FIGS. 3A and 3C, the disposable heat exchanger assembly also comprises a series of disposable bags 4 seal welded to also form a serpentine flow pattern. Refer in FIGS. 3A and 3C to the weld lines X. Also refer to the arrows A2 that depict the serpentine flow path as well as the direction of flow. The disposable bags 4 are joined together via disposable interconnecting tubing 6 in order to form the complete disposable bag manifold assembly 5 such as illustrated in the perspective view of FIG. 3C.

Figure 3A:
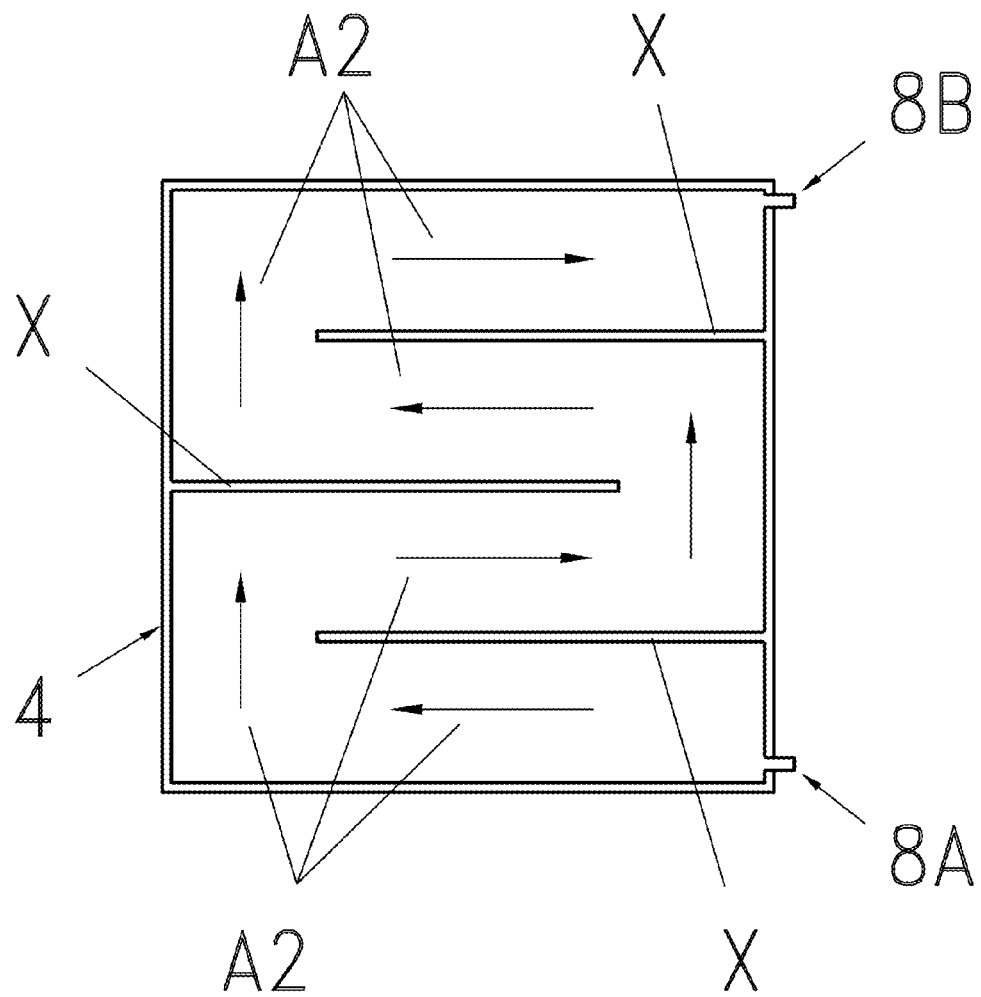
FIG. 3A is a front view of a disposable bag.
Figure 3B:
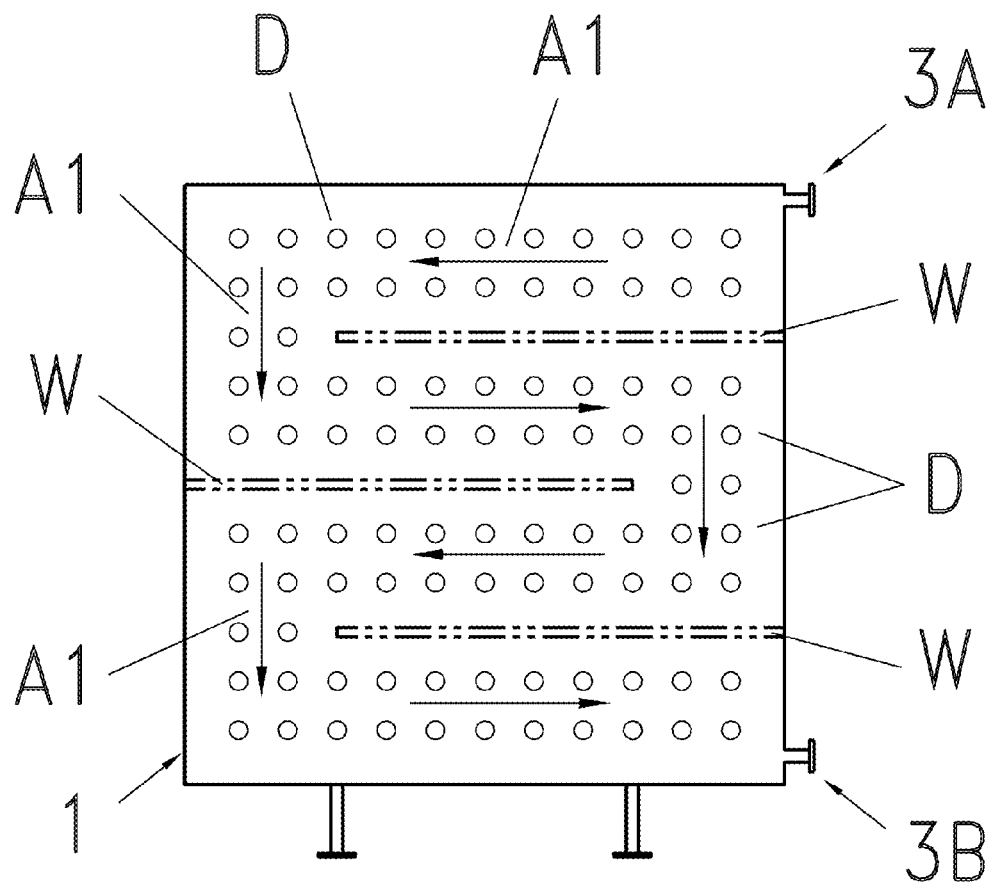
FIG. 3B is a front view of a heat exchanger shell.
Figure 3C:
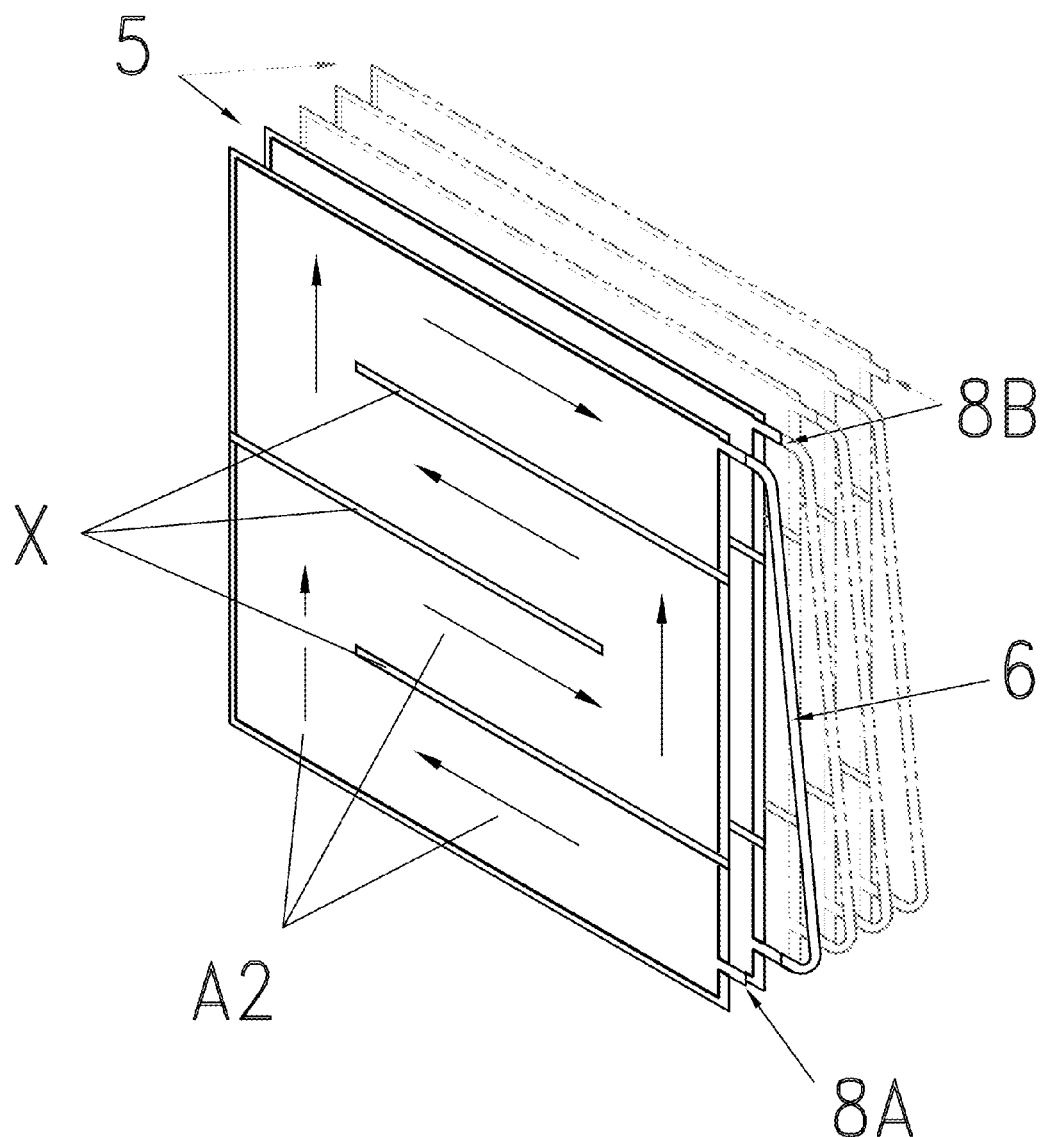
FIG. 3C is a perspective view of a disposable bag manifold assembly with the bags considered as empty.
Figure 3D:
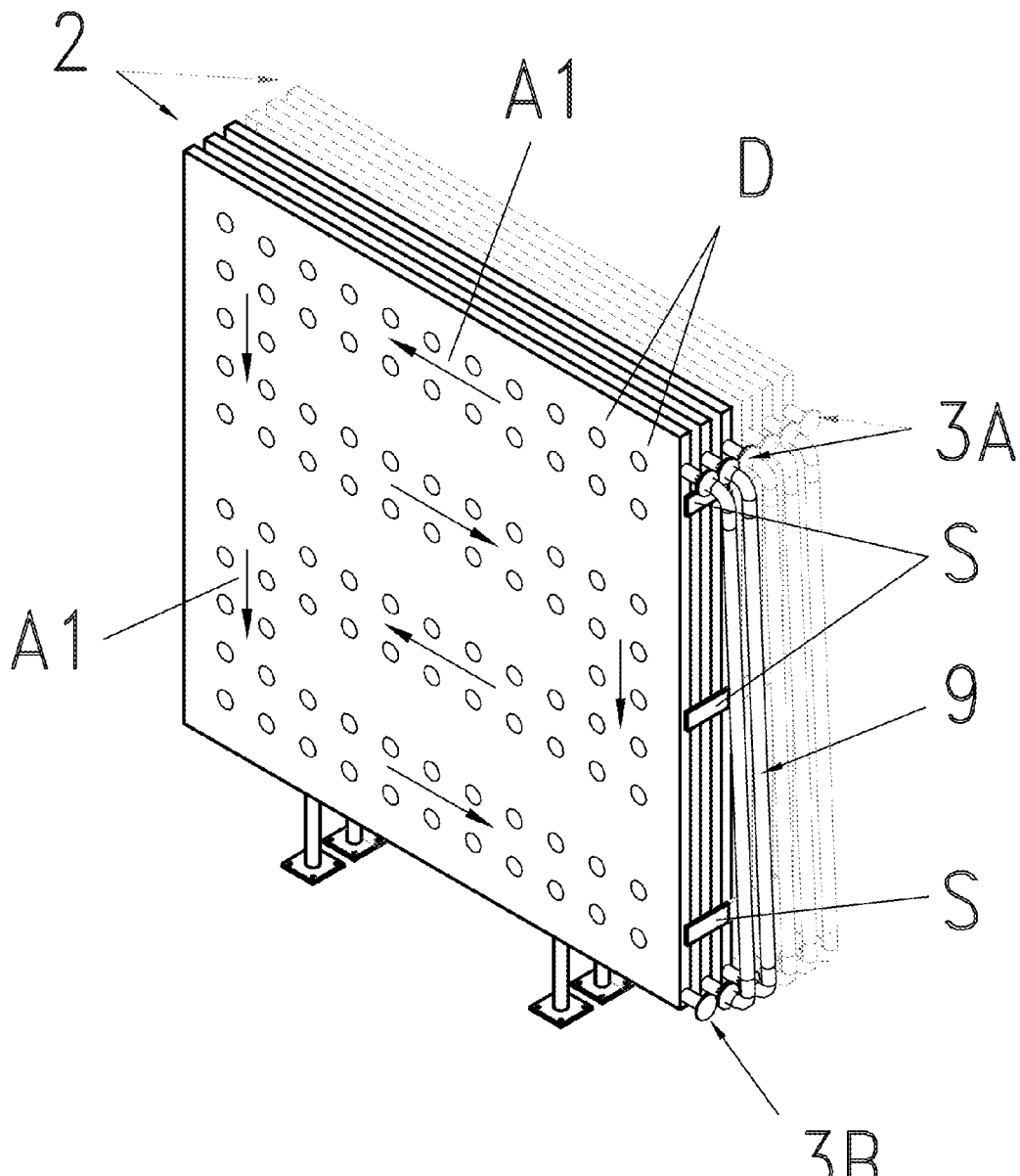
FIG. 3D is a perspective view of a heat exchanger shell manifold assembly.
Figure 3E:
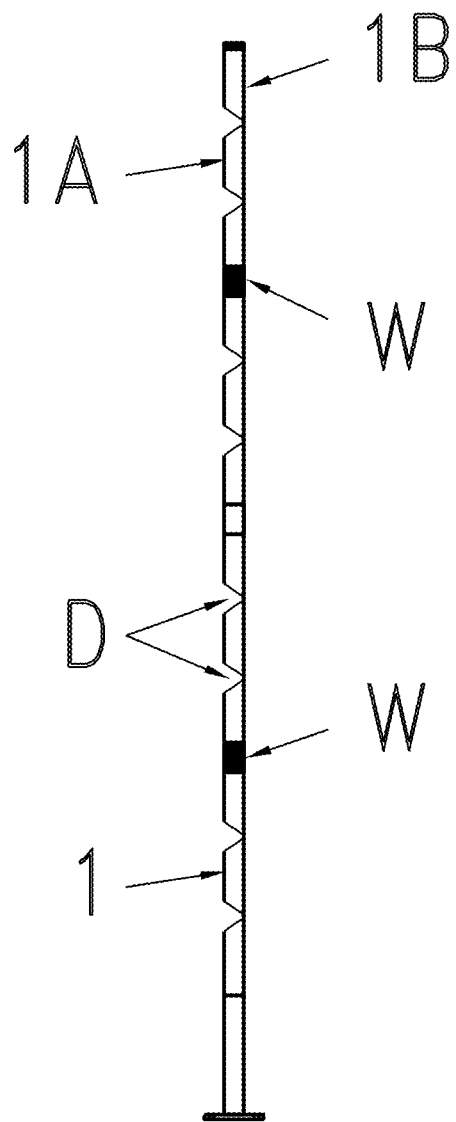
FIG. 3E is a cross-sectional view through one of the plate members.

The cross sectional view in FIG. 3E illustrates the construction of one of the stainless steel plate members 1. Each stainless steel plate member 1 within the heat exchanger shell manifold assembly 2 is comprised of a dimpled heat transfer plate surface 1A on one side spot welded at each dimple D against a flat stainless steel plate 1B on the opposite side. In addition, there are weld seams W, as also illustrated in FIG. 3B between the plates 1A and 1B so as to direct the heating/cooling fluid in the aforementioned serpentine flow path. The dimpled heat transfer surface (plate 1A) and the flat surface (plate 1B) are sealed around all edges with stainless steel. Also, as depicted in FIG. 3D supports S may be provided for holding the plate members in place. Supports S are shown in FIG. 3D on only one side. However, like supports may be provided at other locations between plate members such as at the opposite side thereof. The heating/cooling fluid is therefore allowed to flow between the voids of the dimpled heat transfer and flat stainless steel plates 1A, 1B, and couple from plate member to plate member (via tubing 9).

Figure 3F:
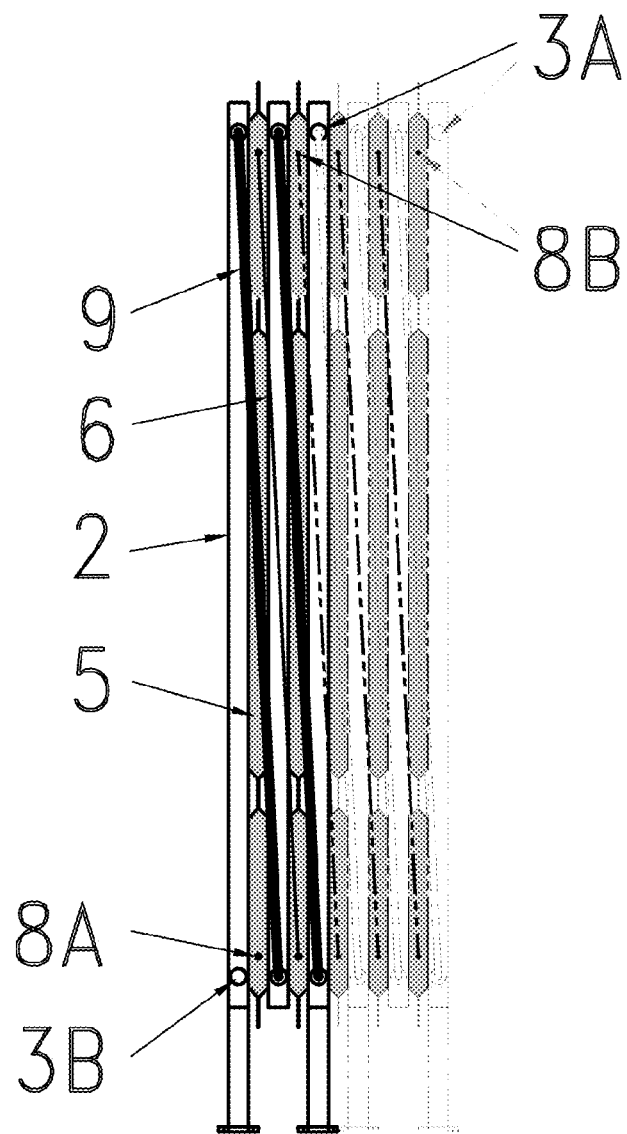
FIG. 3F is a side view of the completed disposable heat exchanger assembly.

Each disposable bag 4 in the disposable bag manifold assembly 5 is intended to be installed between the stainless steel plate members 1 as part of the heat exchanger shell manifold assembly 2. The disposable bag manifold assembly 5 is filled in place where the cell culture or protein purification process fluid enters from the bottom process inlet port 8A of the first disposable bag 4 in the disposable bag manifold assembly 5 series. The process fluid flows from bottom to top in a serpentine pathway to fill the first disposable bag 4 then cascades via interconnecting disposable tubing 6 to the bottom of the second disposable bag 4 in the disposable bag manifold assembly 5. This cascade of filling each disposable bag 4 in series continues through all bags in the custom disposable bag manifold assembly 5 until all disposable bags 4 are filled. The process fluid then exits out the top process outlet port 8B of the last disposable bag 4 in the disposable bag manifold assembly 5. Air is displaced in the disposable bags 4 bottom to top as the bags fill. After all disposable bags 4 are filled, the flow of the process fluid continues in this pattern during normal process operations. FIG. 3F shows the completed assembly with the disposable bags 4 filled and flowing in place and disposed between adjacent plate members. When the disposable bags 4 are full, they form a tight seal between the stainless steel plate members 1 so as to maximize the heat transfer area for efficient heat transfer.

Concurrent with the bags filling and the flow pattern from bottom to top in series within the disposable bag manifold assembly 5, the heating/cooling fluid within the heat exchanger shell manifold flows in a counter-current pattern. The heating/cooling fluid enters the top stainless steel heat transfer fluid inlet port 3A on the last plate in the heat exchanger shell manifold assembly 2. The heat transfer fluid flows through the dimpled stainless steel plate member 1 in a serpentine pathway from top to bottom and cascades to the next plate in the series via the stainless steel interconnecting tubing 9. The flow continues through the entire series of stainless steel plate members 1 and exits out the bottom stainless steel heat transfer outlet port 3B. Preferably, the internal welds within the stainless steel plate members 1 are identical in dimension to the seal welds provided on the disposable bags 4 when filled. The serpentine pathways are hence identical dimensionally but flow in opposite directions to achieve counter-current flow and effective heat transfer. The heat exchanger shell manifold assembly 2 is supported with mechanical plate supports S so that the stainless steel plate members 1 stay rigid such as illustrated in the side view of FIG. 3F.

The heat exchanger shell manifold assembly 2 is intended to be modular for future expansion needs where the heating or cooling load for the intended application changes. FIG. 3D shows a base heat exchanger manifold assembly 2 with a three plate member 1 configuration with an additional three plate members shown in dotted outline for possible future expansion of the heat exchanger. Those skilled in the art will appreciate that the base design does not necessarily need to be a three-plate design if the initial heat transfer area requirement are greater. The heat exchanger shell manifold assembly 2 may be constructed with as many plates as desired to add or remove heat based on the initial application. All heat exchanger manifold shell assemblies 2 are constructed such that additional plates may be added by connecting them with the stainless steel interconnecting tubing 9 via a mechanical joint. The joints may be sanitary, flanged, threaded or weld connections depending on the end user's preference.

To accommodate the modularity of the heat exchanger shell manifold assembly 2, the disposable bag manifold assembly 5 is customized depending on the heat exchanger shell manifold assembly. The disposable bag manifold assembly 5 is configured with as many disposable bags as desired, and as depicted in FIG. 3C. All disposable bag manifold assemblies 5 may be gamma-irradiated for sterility as an assembly once the final configuration is determined. Sterile tube welding or the use of aseptic connection devices at the process inlets and outlets 8 and between the bags at the disposable interconnecting tubing 6 to join multiple sterile bag assemblies is also possible. The disposable tubing manifold assemblies 5 may be configured with heat sealed ends or aseptic connection devices as those skilled in the art can appreciate based on the end user's preference for further expansion options.

The entire heat exchanger as depicted in the drawings, is preferably also covered or surrounded with a certain amount of insulation. This insulation is preferably sealed with a stainless steel sheathing (not shown). The insulation as well as the sheathing is intended to be removable so that it can be placed at each end of the modular heat exchanger shell assembly 2. The insulation may take on many different forms. This may be based on the end user's preference.

The above discussion is meant to be illustrative of the principles and various embodiments of the present invention. Numerous variations and modifications will become apparent to those skilled in the art once the above disclosure is fully appreciated. For example, although various materials have been indicated for purposes of example for use in the present invention, any other suitable materials can be used. In addition, although various plate and bag sizes have been indicated for the purposes of example for use in the present invention, the sizes of the plates and bags may be larger or smaller depending on the end user's heat transfer load requirements and preferred equipment configuration. Mechanical supports for stainless steel plates and supports to aid in the filling of the disposable bags are also customizable depending on the end user's preference. In addition, industries other than biotechnology and pharmaceutical may find appropriate use for the invention herein.

What is claimed is:

1. A disposable heat exchanger assembly, comprising:
a modular stainless steel heating/cooling plate assembly that includes separated plates manifolded together with stainless steel tubing and constructed and arranged in a serpentine flow path for circulation of a heating/cooling fluid; and
a customizable, sterile disposable bag assembly that includes a plurality of bags that are manifolded together with disposable tubing and with each bag having a serpentine flow path therethrough;
the bags being interspersed between the stainless steel heating/cooling plates, wherein a media to be heated/cooled is in said flow path of said bag assembly and is fully contained within said bag assembly such that it does not contact said heating/cooling plate assembly.

2. The disposable heat exchanger assembly of claim 1 wherein the serpentine pattern of the modular stainless steel heating/cooling plate assembly is identical in pattern to the sterile, disposable bags but encased fluids flow in opposite directions to achieve efficient counter-current flow.

3. The disposable heat exchanger assembly of claim 1 wherein the plate assembly is comprised of a series of plate members each including a substantially flat plate disposed in parallel with a dimpled plate.

4. The disposable heat exchanger assembly of claim 3 wherein the plate member also includes seams disposed between the plates for forming the serpentine flow path.

5. The disposable heat exchanger assembly of claim 4 including multiple and parallel disposed seams for directing the serpentine flow.

6. The disposable heat exchanger assembly of claim 1 wherein each bag is also provided with a seal weld to form the serpentine flow path.

7. The disposable heat exchanger assembly of claim 6 wherein the seal weld forms a linear weld line.

8. The disposable heat exchanger assembly of claim 7 wherein there are provided multiple weld lines disposed substantially in parallel to form the serpentine flow path.

9. The disposable heat exchanger assembly of claim 6 wherein the plate assembly is comprised of a series of plate members and each bag is disposed between adjacent plate members, and further including tubing that connects from one bag to an adjacent bag, and tubing that connects from one plate member to an adjacent plate member, so that flow is from one bag to an adjacent bag and from one plate member to an adjacent plate member.

10. A heat exchanger assembly for controlling the temperature of fluid flowing through the assembly, said heat exchanger assembly comprising:
- a plurality of plate members each comprised of spaced apart plates that define a flow path therebetween;
- a plurality of bags through which a fluid to be processed passes;
- said bags being disposed between adjacent plate members;
- said plate members interconnected so that heating/cooling fluid flowing therethrough couples from plate member to plate member;
- said bags interconnected so that media to be heated/cooled flowing therethrough couples from bag to bag, wherein said media in said flow path of said bag assembly is fully contained within said bag assembly such that it does not contact said plate members;
- said plate members interconnected so that the flow therethrough is in a serpentine flow path;
- said bags interconnected so that the flow therethrough is in a serpentine flow path;
- the direction of flow in the respective plate members and bags being reversed from each other.

11. The heat exchanger assembly of claim 10 wherein flow through the plate members is from the top to the bottom thereof.

12. The heat exchanger assembly of claim 11 wherein the flow through the bags is from bottom to top thereof.

13. The heat exchanger assembly of claim 10 wherein each plate member each includes a substantially flat plate disposed in parallel with a dimpled plate.

14. The heat exchanger assembly of claim 13 wherein the plate member also includes seams disposed between the plates for forming the serpentine flow path.

15. The heat exchanger assembly of claim 14 including multiple and parallel disposed seams for directing the serpentine flow.

16. The heat exchanger assembly of claim 15 wherein each bag is also provided with a seal weld to form the serpentine flow path.

17. The heat exchanger assembly of claim 16 wherein the seal weld forms a linear weld line.

18. The heat exchanger assembly of claim 17 wherein there are provided multiple weld lines disposed substantially in parallel to form the serpentine flow path.

19. The heat exchanger assembly of claim 10 further including tubing that connects from one bag to an adjacent bag, and tubing that connects from one plate member to an adjacent plate member, so that flow is from one bag to an adjacent bag and from one plate member to an adjacent plate member.

* * * * *